United States Patent [19]

Kondo et al.

[11] 4,270,920

[45] Jun. 2, 1981

[54] INTEGRATED MATERIAL FOR CHEMICAL ANALYSIS AND A METHOD OF USING THE SAME

[75] Inventors: Asaji Kondo; Fuminori Arai; Masao Kitajima, all of Asaka, Japan

[73] Assignee: Fuji Photo Film Co., Ltd., Minami-ashigara, Japan

[21] Appl. No.: 71,618

[22] Filed: Aug. 31, 1979

[30] Foreign Application Priority Data

Aug. 31, 1978 [JP] Japan .............................. 53-106850

[51] Int. Cl.³ .................. G01N 33/52; G01N 33/62; G01N 33/66; G01N 33/72
[52] U.S. Cl. .................................. 23/230 B; 23/901; 23/902; 23/905; 23/909; 23/924; 435/22
[58] Field of Search .................. 23/230 B; 422/56, 57

[56] References Cited

U.S. PATENT DOCUMENTS

| | | | |
|---|---|---|---|
| 3,006,735 | 10/1961 | Jordan | 422/56 X |
| 3,139,328 | 6/1964 | Jacob | 422/56 |
| 4,046,512 | 9/1977 | Kaczmarek | 23/232 R X |
| 4,050,898 | 9/1977 | Goffe | 422/57 |

*Primary Examiner*—Sidney Marantz
*Attorney, Agent, or Firm*—Sughrue, Rothwell, Mion, Zinn and Macpeak

[57] ABSTRACT

An integrated material for chemical analysis comprising three or more reagent layer units on a support and a porous spreading layer, said units containing reagents for different chemical analyses and being proximately arranged on a support such that approximately equal portions thereof are within a spreading circle defined by the diffusion of a liquid sample as it passes through the porous spreading layer, and a method for analyzing blood using the same.

26 Claims, 7 Drawing Figures

INTEGRATED MATERIAL FOR CHEMICAL ANALYSIS AND A METHOD OF USING THE SAME

BACKGROUND OF THE INVENTION

1. Field of the Invention

The present invention relates to an integrated material comprising reagent layer units for chemical analysis and a method of using the same. More particularly, the present invention relates to a material capable of performing a plurality of chemical analyses at one time. Still more particularly, the present invention relates to an integrated material in which a plurality of units containing different reagents for chemical analysis are proximately arranged on a support so that at least a portion of their reagent layer units are in contact with each other or in close vicinity to one another within a spreading circle defined by the diffusion of an assay sample as it passes through a porous spreading layer.

2. Description of the Prior Art

As materials for simple and rapid dry chemical analyses of liquid samples, sheet-like multilayered materials for chemical analysis have been disclosed in U.S. Pat. Nos. 3,526,480, 3,663,374, 3,992,158, 4,042,355, 4,066,403 and 4,050,898 and collected papers (pp. 13, 14, 47, 76 and 118) for the 10th International Conference of Clinical Chemistry (Mexico City, 2/26–3/3/78). Such multilayered materials for chemical analysis are based on the idea of providing a thin film containing a reagent for the analysis in a binder such as gelatin beforehand, and on chemical analysis a drop of liquid sample to be tested is applied to the sheet. The reagent layer contains a system which, upon reacting with a particular component in the sample liquid, leads to color development, coloration or discoloration. The content of the particular component in the sample liquid corresponds to the color density and quantitative analysis is possible by optical analysis chiefly by colorimetry. Unlike the conventional methods, these materials are dry materials for chemical analysis and eliminate the need for reagent solutions and test tubes.

The fundamental construction of these multilayered materials for chemical analysis is a combination of a porous spreading layer and a reagent layer, and the reagent layer is sometimes provided as a multilayered unit by dividing its functions between, for example, a first reagent layer and a second reagent layer or between a reagent layer and a color developing, a color detecting or a color receiving layer. Sometimes an intermediate layer such as a radiation-blocking layer or a barrier layer is placed between such a plurality of the reagent layers. Alternatively, there is provided a construction in which the spreading layer includes a reagent and spreading and the reaction upon which the analysis is based are integrated. In any case, it is basic that the layer construction comprises two functional layers, i.e., a spreading layer and a reagent layer. A liquid sample dropped on such a multilayered material for chemical analysis diffuses uniformly throughout the porous spreading layer and permeates into the reagent layer when it reacts with the reagents contained therein.

The above-mentioned multilayered materials for chemical analysis are very suitable for a simple and rapid chemical assay of liquid samples containing many components such as saliva, blood, urine, etc., in a dry state operation using no test tubes or reagent solutions. Such a material requires analytical reagents for the specific items to be analyzed, for example, reagents for the quantitative assay of blood for glucose, urea nitrogen and amylase. Therefore, when six times, e.g., bilirubin, albumin and cholesterol in addition to the above three are to be quantitatively analyzed, it is necessary to choose six different multilayered materials for each chemical analysis and to apply a drop of whole blood or serum in an amount of 5 to 15 µl on each material, after which, upon completion of each color development reaction, colorimetric analyses of the respective materials are conducted.

The above-mentioned multilayered materials for chemical analysis are quite excellent with respect to the simplicity of the quantitative analysis, and when used for the purpose of the chemical analysis of blood, these materials are very convenient for analyzing one item per patient. However, it is common practice in clinical chemistry examinations to test 5 to 10 items on each blood sample collected from each patient. Therefore, in order to utilize the above-mentioned multilayered materials for the chemical analysis for that purpose, there is involved the relatively complicated procedure of choosing an analytical material for each of the 5 to 10 items tested, number them and apply a drop of the blood on each material. Further, when conducting tests on many persons (as would be the case in a hospital), selection of the analytical materials, numbering, repetition of application, etc., amount to an enormous amount of work. In this respect, efforts have been made to minimize the number of such repetitions and it has been discovered that by using an integrated material constructed such that the necessary number of reagents for each chemical analysis are incorporated in a specific arrangement, e.g., radially on a support, and applying the sample to be tested at a centrally located point such that the sample diffuses to each analytical material, the analysis is simplified.

SUMMARY OF THE INVENTION

An object of the present invention is to provide an integrated material comprising reagent layer units for chemical analysis which permits three or more chemical analyses with one analytical element and one application of liquid sample.

Another object of the present invention is to provide an integrated material comprising reagent layer units for the chemical analysis which permits three or more chemical analyses under the identical conditions with one analytical element and one application of a liquid sample.

A further object of the present invention is to provide a method of using an integrated material comprising a plurality of reagent layer units for chemical analysis of three or more tests with one analytical element and one application of a liquid sample.

Still a further object of the present invention is to provide a method of using an integrated material comprising reagent layer units for the chemical analysis which permits three or more chemical analyses or tests under identical conditions with one analytical element and one application of a liquid sample.

The present invention provides an integrated material for chemical analysis comprising three or more reagent layer units for chemical analysis on a support and a porous spreading layer, each of the reagent layer units containing a reagent for a different chemical analysis or test and is proximately arranged in contact with or in close vicinity to another. The present invention also provides a method for using an integrated material comprising applying a liquid sample to the aforementioned spreading layer(s) whereby the liquid sample is spread by the spreading layer(s) and penetrates to each of the reagent layer units and a method for analyzing blood using the same.

DETAILED DESCRIPTION OF THE INVENTION

Figure 1:
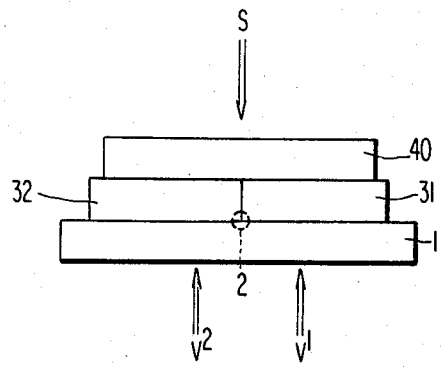
FIG. 1 is a cross-section of the fundamental construction of an integrated material comprising reagent layer units for chemical analysis.

An essential feature of the integrated material of the present invention is that the reagent layer units are arranged in contact with or in close vicinity to one another. This means that the reagent layer units are arranged in such way that at least a portion of each is in contact with or in close vicinity to each other in the area in which a liquid sample applied on a porous spreading layer is spread as it passes through the spreading layer and can reach the reagent layers. Preferably, it means that in the area in which a liquid sample is applied on a porous spreading layer at a centrally located point (hereafter the "center point") above the surface of a support is spread by the spreading layer and reaches the reagent layers, the reagent layer units are arranged in such way that at least a portion (e.g., an edge) of each is in contact with or in close vicinity to the others so as to provide reagent layer units having a sufficient test area to permit the chemical analysis by the colorimetric analysis (hereinafter referred to as the "chemical analysis region"). If the porous spreading layer is of a single continuous and substantially isotropic structure, a line connecting the furthest points which the liquid sample applied to the center point reaches upon passing through the spreading layer will form the circumference of a closed circle or a nearly circular figure (the spreading circle), the center of which is approximately the center point as defined above. Preferably equal portions of each reagent layer unit are within the spreading circle.

As the amount of the liquid sample applied is increased, the spreading circle becomes larger in proportion to the amount with almost no limitation, and within the spreading circle, the liquid sample reaches the reagent layers but the time for the liquid sample to be spread increases roughly in proportion to the diameter of the circle. However, in chemical analysis using the integrated material comprising the analytical materials in accordance with the present invention, the amount of the liquid sample applied is limited to a small amount chiefly to simplify operations and to reduce the time necessary for the series of operations required for analysis (e.g., the time from application of the liquid sample to the completion of the chemical analysis). For such practical reasons, the radius of the spreading circle is about 3 to 30 mm, and preferably about 3 to 20 mm, and the chemical analysis region must exist within the spreading circle. Therefore, the reagent layer units for chemical analysis can be arranged so that the analysis region is present within a circle of a radius of up to about 30 mm, and preferably up to about 20 mm around the center point.

Examples of the arrangement of three or more different reagent layer units for the chemical analysis having a specific shape are a radial arrangement in which the apex of a sector or each polygon (e.g., triangle, rhombus, rectangle, square, etc.) is in contact with one another at the center point or is within a circle of a specific radius around the center point; an arrangement in which polygons, circles, ellipses, ovoid figures, etc., are within a circle of a specific radius around the center point; a checkered pattern arrangement within a circle having a specific radius around the center point; and an irregular arrangement within a circle having a specific radius around the center point. The above-mentioned circle having a specific radius is a circle equal to or smaller than the spreading circle. Among these arrangements, the first two are preferred because the liquid sample spread by the porous spreading layer reaches the reagent layers at the same distance from the center point at which the liquid sample is applied especially with good uniformity (that is, the amounts of the liquid sample per unit area are the same).

The number of the reagent layer units for the chemical analysis to be incorporated in the integrated material in accordance with the present invention is three or more, and preferably four or more. In general, the greater the number is the better.

As the support, a sheet or a laminated sheet of a thickness of about 10 μm to about 0.5 mm, preferably about 20 μm to about 0.3 mm, made of a material having a good transparency in the near ultraviolet light, visible and near infrared regions such as polyesters (e.g., polyethylene terephthalate), polycarbonates of bisphenol, cellulose esters (e.g., cellulose diacetate, cellulose triacetate, cellulose acetate propionate, cellulose acetate butyrate, cellulose nitrate), cellophane, polystyrene, polyolefins (e.g., polyethylene, polypropylene), halogen-containing vinyl polymers (e.g., polyvinyl chloride, polyvinylidene chloride) or organic or inorganic glass. The support can be provided with a frame entirely or partially on the periphery. If the above-mentioned supports or other supports (e.g., translucent or opaque supports such as of paper, plastic, metal foil, etc.) coated with a very thin film of a release agent such as silicone resin, etc., are used as the support, it provides the protection and it can be removed by peel-off just before the analysis measurement. When such a removable support is employed, it is preferred to provide a single porous spreading layer common to the respective reagent layer units capable of supporting structure of the integrated material. Each of the reagent layer units may contain an individual support or the units can share a common support.

The construction and preparation of the support, reagent layer, or in the case of dividing the function of the reagent layer, the first reagent layer, second reagent layer, color development layer, color detecting layer, color receiving layer, radiation-blocking layer, barrier layer, etc., and the method of incorporating these layers into the reagent layer units for chemical analysis can be practiced according to the description in the above-mentioned patent specifications.

The radiation-blocking layer is preferably a water-permeable radiation-blocking layer made of a porous metal film or a water-permeable radiation-blocking layer containing a metal powder. The construction of such radiation-blocking layers, their preparation and incorporation into multilayered materials for chemical analysis can be practiced according to the descriptions of Japanese patent application Nos. 98900/78 and 98902/78 and U.S. Pat. Nos. 4,042,335 and 4,144,306.

The fundamental construction of the integrated material comprising multilayered materials for chemical analysis in accordance with the present invention is shown in FIG. 1 and is composed of three components: a support 1, overlaying reagent layer units 31 and 32 arranged in contact with or in close vicinity to each other around the center point 2 on the support and a porous spreading layer 40 laminated and fixed into an integrated form. The reagent layer units 31 and 32 can be in contact with each other at the point 2 as the boundary or can be set apart by a certain distance from (that is, in close vicinity to) each other.

The porous spreading layer 40 can have a unitary construction common to the reagent layer units 31 and 32 or it can be divided into a plurality of members corresponding to each of the respective reagent layer units. It is preferred to employ a common unitary porous spreading layer. This is because when the liquid sample is spread (passes) through the porous spreading layer of the unitary construction, the spread of the liquid sample is substantially uniform, thus rendering the chemical analysis more accurate.

On the porous spreading layer (i.e., on the surface distant from the reagent layer) can be provided a waterproof layer having at least one small opening as described in Japanese Utility Model Application No. 59888/78, a water evaporation inhibiting layer described in Japanese Utility Model Application No. 59886/78 or 59887/78, or a combination of a filter layer to filter definitely-shaped components of blood described in Japanese Utility Model Application No. 77177/78 and the waterproof layer having at least one small opening (with the waterproof layer contact with the porous spreading layer).

While the method of forming a plurality of different reagent layer units for chemical analysis on the support may be effected by patching, i.e., cutting different, ready-made reagent layers for chemical analysis into shapes of, e.g., circles, sectors or polygons and arranging and bonding them on the support, or by forming a plurality of different reagent layers on the support by spot-coating or patching thereafter laminating and bonding the porous spreading layer thereon, the actual method can be freely chosen depending on the number of the items to be analyzed, the amount of production, the cost, etc. Further, as a means to distinguish the direction of the reagent layer units applied to the integrated or to identify the multilayered materials arranged on the integrated material, it is possible to make each of the plurality of different multilayered materials for chemical analysis look different by changing the center angle in the case of sectors or the size or shape in the case of circles or polygons.

In using the integrated material comprising reagent layer units for chemical analysis, first, a liquid sample is applied onto the porous spreading layer. The point of application is on the upper surface at or in the vicinity of the center point. The means of application include pressing or spreading of a liquid sample, spraying of a liquid sample, etc., including all manners and processes as well as such manner and process as indirectly applying a liquid sample to the porous spreading layer via another layer(s) overlaying the porous spreading layer. Where the integrated material of the present invention is provided with a waterproof layer having at least one small opening or a filter layer as the top layer by applying the sample to the small opening of the waterproof layer or to the filter layer at the point above the center point, the sample can pass through the small opening in the filter layer (any definitely-shaped components, if present, being filtered off) and reach the porous spreading layer. More particularly, the liquid sample is applied from above in the direction designated S at the center point (the point 2 in FIG. 1) or in the vicinity of the center point so that, by a single application of the liquid sample, the sample spread by the porous spreading layer is substantially uniformly spread over at least the respective reagent layers of the plurality of the different reagent layer units for chemical analysis arranged on the support. A single application of the liquid sample is adequate. The liquid sample thus applied is spread by the respective porous spreading layers of the respective reagent layer units for chemical analysis or by the common porous spreading layer and reaches each reagent layer. Thereafter it is spread throughout each reagent layer unit where the liquid sample reacts with each reagent contained therein to effect the color development or discoloration (hereinafter both referred to as "color development"). After substantially completing the color development, each color concentration can be measured from the directions $V^1$ and $V^2$ in turn to quantitatively analyze the respective chemical components in the liquid sample.

As having been clarified by the foregoing explanation, the method of using the integrated material in accordance with the present invention and applying a liquid sample one time has a remarkably excellent feature that the application or arrival of the liquid sample at each reagent layer unit is effected under identical conditions in each material, which means this method substantially eliminates or greatly reduces possible error factors inevitably accompanying the quantitative analysis using each material for chemical analysis.

The method of using the integrated material in accordance with the present invention can be extended to using a material for chemical analysis having two or more different reagent layer units and a common or individual porous spreading layers on a single support. In other words, if the material for chemical analysis, although not designed for practicing three or more items of chemical analyses by a single application of a liquid sample like the integrated material of the present invention, is so constructed that the analysis regions of the reagent layer units and the porous spreading layer are arranged within the spreading circle, then the method of the present invention can be extended to such a material. Especially, in the materials for chemical analysis in which two different reagent layer units are arranged in contact with or in close vicinity to each other, the method of the present invention can be practiced by applying a liquid sample on the porous spreading layer at a point along the line of contact of the two different reagent layers, e.g., the center of symmetry of the respective analysis region in the two reagent layers or its vicinity.

The representative embodiments of the integrated material comprising multilayered materials for chemical analysis in accordance with the present invention are schematically illustrated in FIGS. 2 through 5.

Figure 2:
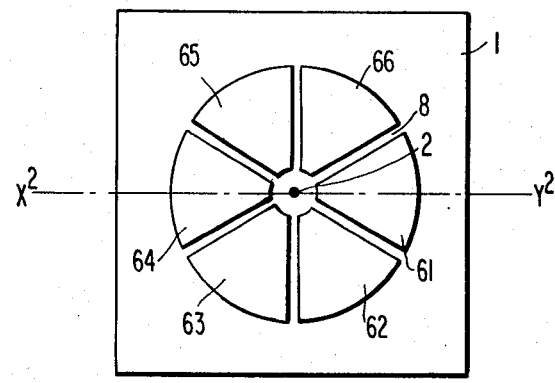
FIG. 2 shows an integrated material comprising reagent layer units for chemical analysis in which six different multilayered materials are radially arranged in close proximity to one another so that they circumscribe a small circle having its center at the center point of the support.
Figure 3:
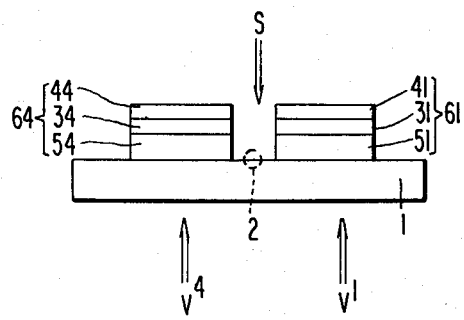
FIG. 3 is its cross-section along the broken line $X^2$—$Y^2$.

FIGS. 2 and 3 show an example of an integrated structure in which six different reagent layer units for chemical analysis each consisting of a reagent layer and a porous spreading layer in the shape of a sector are arranged radially with their points at the center point and in close vicinity to one another. FIG. 2 is the top view of the above structure in which six different finished reagent layer units for chemical analysis 61 through 66 cut in the shape trapezoids or sectors are arranged and bonded radially around the center point 2 on a transparent support 1 so that one end of each material for chemical analysis is present within a circle 4 mm in radius around the center point 2. The six reagent layer units may be arranged without any space therebetween or as shown in the Figure with a space 8 of about 0.5 to 5 mm therebetween. The spaces between the respective materials for the analysis and the central part of radial arrangement may be treated to render them waterproof or water repellent.

FIG. 3 is a schematic cross-section, along the broken line $X^2$—$Y^2$ of the integrated material of FIG. 2. The different reagent layer units for the analysis 61 and 64 are arranged around the center point 2 on the transparent support 1. The units 61 and 64 are illustrated as having transparent supports 51 and 54, reagent layers 31 and 34 and porous spreading layers 41 and 44, respectively. The transparent supports 51 and 54 can be omitted. On the center point 2 is applied 50 to 90 μl of a liquid sample from the direction S. The color densities due to the color developments in the reagent layers in the respective materials are measured from the directions $V^1$ and $V^4$ in turn by the quantitative colorimetry. The support is flat in principle, but may be conical with the center point either as the top or the bottom. The materials for the support are most preferably a transparent organic or inorganic glass or photographic (plastic) film base. Alternatively, a mere soft transparent film or a thin soft transparent film with a frame may also be employed, or the support may be provided on the spreading layer, but in this case the direction of application is opposite the direction S.

Figure 4:
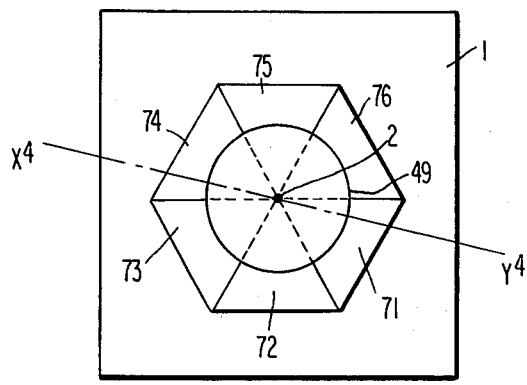
FIG. 4 shows an integrated material comprising reagent layer units for chemical analysis in which six different unfinished reagent layer units for chemical analysis are radially arranged around the center point on a support and in contact with one another thereafter a single common spreading layer is laminated.
Figure 5:
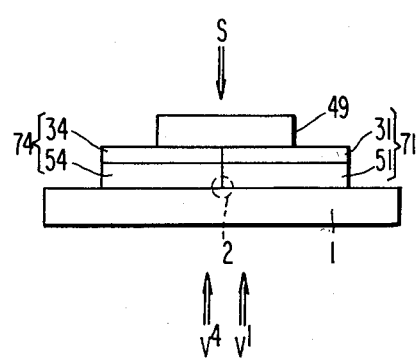
FIG. 5 is a cross-section along the broken line $X^4$—$Y^4$ in FIG. 4.

FIGS. 4 and 5 show an integrated structure in which triangular shaped reagent layer units for chemical analysis without the spreading layers laminated thereto, i.e., those consisting of reagent layers or reagent layers plus supports, are arranged and integrated radially around the center point 2 and in contact with one another by coating or patching, and then a circular porous spreading layer is laminated thereon concentric with the center point and thereafter fixed together. FIG. 4 is the top plan view of such a structure. First, around the center point 2 on a support board 1 are radially arranged and fixed six regular triangular shaped reagent layer units for chemical analysis 71 through 76 with the corners in contact with one another. Next, a single porous spreading layer 49 in the form of a circle or polygon having a radius of about 1.5 to 4 cm around the center point is laminated and fixed thereon to form a porous spreading layer common to the six reagent layer units for chemical analysis, thus completing the integrated structure.

FIG. 5 is a schematic cross-section along the broken line $X^4$—$Y^4$ of the above structure of FIG. 4.

There are reagent layer units for chemical analysis 71 and 74 consisting of transparent supports 51 and 54 and reagent layers 31 and 34 (not containing porous spreading layers) on a support 1, on which a porous spreading layer 49 common to both materials is laminated and bonded to complete the integrated material for chemical analysis.

In a manner similar to the case of the integrated material in FIG. 2, the application of a liquid sample is conducted from the direction S and the quantitative colorimetric analysis is performed from the directions $V^1$ and $V^4$. Here it is also possible to form a structure without supports 51 and 54 for the respective materials, i.e., a structure in which various triangular shaped reagent layer units are radially arranged in contact with one another between the common support and the common porous spreading layer. Furthermore, in FIG. 1, the structure in which the support 1 has been moved from its original position onto the spreading layer 49 is also feasible. In this case, the support must have proper small opening(s) above the center point 2 to let the applied liquid sample pass.

Figure 6:
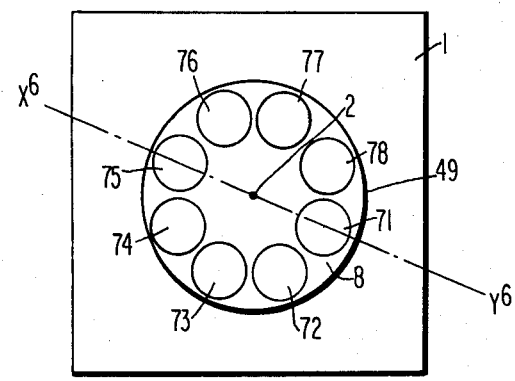
FIG. 6 shows an integrated material comprising reagent layer units for chemical analysis in which eight different circular reagent layers are arranged so as to be inscribed in a circle of a specific radius around the center point on a support and thereafter a common circular spreading layer is laminated thereon.
Figure 7:
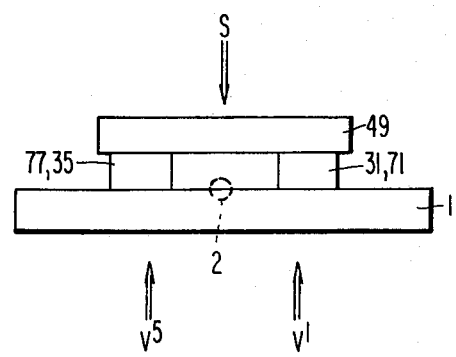
FIG. 7 is a cross-section along the broken line $X^6$—$Y^6$ in FIG. 6.

FIGS. 6 and 7 show another example of the integrated material. In this example, eight circular reagent layers 71 through 78 are arranged apart from one another on a support so that all the circles are circumscribed by a circle having a specific radius around the center point 2, and a single circular porous spreading layer 49 is provided thereon. FIG. 6 is a planar view of this integrated material and FIG. 7 is a schematic cross-section along the broken line $X^6$—$Y^6$ of FIG. 6. A liquid sample is applied to the porous spreading layer 49 at the point above the center point 2 from the direction S and the quantitative colorimetric analysis is conducted from the directions $V^1$ and $V^5$.

While the present invention has been described for integrated material constructed using six and eight reagent layer units for chemical analysis, needless to say, it is possible to construct integrated material of the present invention using three or more reagent layer units for chemical analysis.

The features of the integrated materials for chemical analysis in accordance with the present invention as compared with the conventional multilayered materials for chemical analysis are as follows.

First, conventional multilayered materials for chemical analysis require one analysis material per test item, it is therefore necessary to choose and number a plurality of analysis material. In contrast, since the integrated materials in accordance with the present invention have a set of the necessary number of analysis materials arranged on a single support respectively, they greatly save trouble in selection and numbering and in addition they are so compact to save storage space.

While conventional multilayered materials require individual applications of a liquid sample for each item to be analyzed, which means it is necessary to apply liquid samples the number of times corresponding to the number of items to be analyzed, the integrated materials in accordance with the present invention permit a number of analyses with a single application of liquid sample. Thus, the analytical operation is much more simplified and there is less possibility of operational errors. In addition, when automation of application is adopted, the system of the present invention is much simpler to use as compared with the conventional systems.

Especially when the integrated materials are used in the field of the chemical analysis of blood, by making available a sheet having the reagent layer units for the chemical analysis designed for analyzing a plurality of items necessary for urgent assay, it is possible to conduct the necessary number assays in a short time using such a sheet and by a single application of a blood sample. Therefore, it provides a very useful analyzing means for emergency use.

While the invention has been described in detail and with reference to specific embodiments thereof, it will be apparent to one skilled in the art that various changes and modifications can be made therein without departing from the spirit and scope thereof.

What is claimed is:

1. An integrated material for chemical analysis comprising three or more reagent layer units on a support and a porous spreading layer, said units containing reagents for different chemical analyses and being proximately arranged on a support such that approximately equal portions thereof are within a spreading circle defined by the diffusion of a liquid sample as it passes through the porous spreading layer.

2. The integrated material of claim 1, wherein said reagent layer units are in the shape of sectors radially arranged around the center of the spreading circle.

3. The integrated material of claim 2, wherein said sectors are in radial contact with one another.

4. The integrated material of claim 1, wherein said reagent layer units are in the shape of triangles radially arranged around the center of the spreading circle.

5. The integrated material of claim 4, wherein said triangles are in radial contact with one another.

6. The integrated material of claim 1, wherein said reagent layer units are in the shape of circles radially arranged around the center of the spreading circle.

7. The integrated material of claim 1, wherein said reagent layer units have different shapes such that they can be easily identified from one another.

8. The integrated material of claim 1, wherein said reagent layer units are in contact with one another and located entirely within the spreading circle.

9. The integrated material of claim 1, wherein said reagent layer units have equal areas.

10. The integrated material of claim 1, wherein said porous spreading layer is divided into porous spreading layer units corresponding to each of the reagent layer units.

11. The integrated material of claim 1, which additionally comprises a filter layer.

12. The integrated material of claim 1, wherein said material additionally comprises a waterproof layer having at least one opening therein.

13. The integrated material of claim 12, wherein said opening corresponds to the center of the spreading circle.

14. The integrated material of claim 1, wherein said material additionally comprises a radiation-blocking layer.

15. The integrated material of claim 1, wherein at least one of said reagent layer units contains a reagent for the analysis of glucose, urea nitrogen, amylase, bilirubin, albumin, and cholesterol.

16. The integrated material of claim 1, wherein said reagent layer units contain reagents which react with chemical components of the liquid test sample to cause a change in the color value of the reagent layer.

17. A method of chemical analysis which comprises applying one or more drops of a liquid test sample to the spreading layer of an integrated material for chemical analysis comprising three or more reagent layer units on a support and a porous spreading layer, said units containing reagents for different chemical analyses and being proximately arranged on a support such that approximately equal portions thereof are within a spreading circle defined by the diffusion of a liquid sample as it passes through the porous spreading layer, and colorimetrically analyzing said reagent layer units.

18. A method for chemically analyzing blood which comprises applying a sample of blood to the porous spreading layer of an integrated material for chemical analysis comprising three or more reagent layer units on a support and a porous spreading layer, said units containing reagents for different chemical analyses and being proximately arranged on a support such that approximately equal portions thereof are within a spreading circle defined by the diffusion of a liquid sample as it passes through the porous spreading layer, and colorimetrically analyzing said reagent layer units.

19. The method of claim 18, wherein said sample is a sample of whole blood.

20. The method of claim 18, wherein said reagent layer units contain reagents which react with chemical components of the blood to produce a change in the color value of the reagent layer.

21. An integrated material for chemical analysis comprising in order on a support, three or more reagent layer units, a unitary, porous spreading layer overlaying each of said units, and a waterproof layer having at least one opening therein overlaying said spreading layer, each of said units containing a reagent for a different chemical analysis and being proximately arranged on a support such that approximately equal portions thereof are within a spreading circle defined by the diffusion of a liquid sample as it passes through the porous spreading layer.

22. The integrated material of claim 21 wherein a single centrally located opening is present in said waterproof layer.

23. The integrated material of claim 22 wherein said reagent layer units are in the shape of sectors radially arranged around the center of the spreading circle.

24. A method of chemical analysis which comprises applying one or more drops of a liquid test sample to the spreading layer of an integrated material for chemical analysis comprising in order on a support, three or more reagent layer units, a unitary, porous spreading layer overlaying each of said units, and a waterproof layer having at least one opening therein overlaying said spreading layer, each of said units containing a reagent for a different chemical analysis and being proximately arranged on the support such that approximately equal portions thereof are within a spreading circle defined by the diffusion of a liquid sample as it passes through the porous spreading layer, and colorimetrically analyzing said reagent layer units.

25. The method of claim 24 wherein a single centrally located opening is present in said said waterproof layer.

26. The method of claim 25 wherein said reagent layer units are in the shape of sectors radially arranged around the center of the spreading circule.

* * * * *